United States Patent [19]
Strobl et al.

[11] Patent Number: 5,547,456
[45] Date of Patent: Aug. 20, 1996

[54] VENT SYSTEM FOR ENDOSCOPES

[75] Inventors: Karlheinz Strobl; Steven Metras, both of Charlton, Mass.

[73] Assignee: Karl Storz GmbH & Co., Germany

[21] Appl. No.: 377,538

[22] Filed: Jan. 24, 1995

[51] Int. Cl.⁶ .................... A61B 1/04; A61B 1/12
[52] U.S. Cl. ............. 600/133; 600/159; 600/121
[58] Field of Search .................... 600/101, 121, 600/133, 159, 155, 156, 122, 123, 124, 125

[56] References Cited

U.S. PATENT DOCUMENTS

| | | | |
|---|---|---|---|
| 4,878,484 | 11/1989 | Miyagi | 128/4 |
| 5,343,854 | 9/1994 | Katsurada | 128/4 |
| 5,356,376 | 10/1994 | Milijasevic et al. | 604/30 |

FOREIGN PATENT DOCUMENTS

| | | | |
|---|---|---|---|
| 112802 | 4/1989 | Japan | 128/4 |

*Primary Examiner*—Richard J. Apley
*Assistant Examiner*—Beverly M. Flanagan
*Attorney, Agent, or Firm*—Donald D. Mon

[57] ABSTRACT

A continuous vent for an endoscope which always allows flow of gas in order to prevent damaging differential pressures and always prevents entry of liquid into the endoscope. A barrier for this purpose overlays a vent port and is held in place by a ring-shaped spacer which with an overhanging shoulder leaves a limited space for flow of fluid and excludes most particulates from the barrier. The barrier maybe an assortment of hydrophobic and hydrophilic layers.

2 Claims, 1 Drawing Sheet

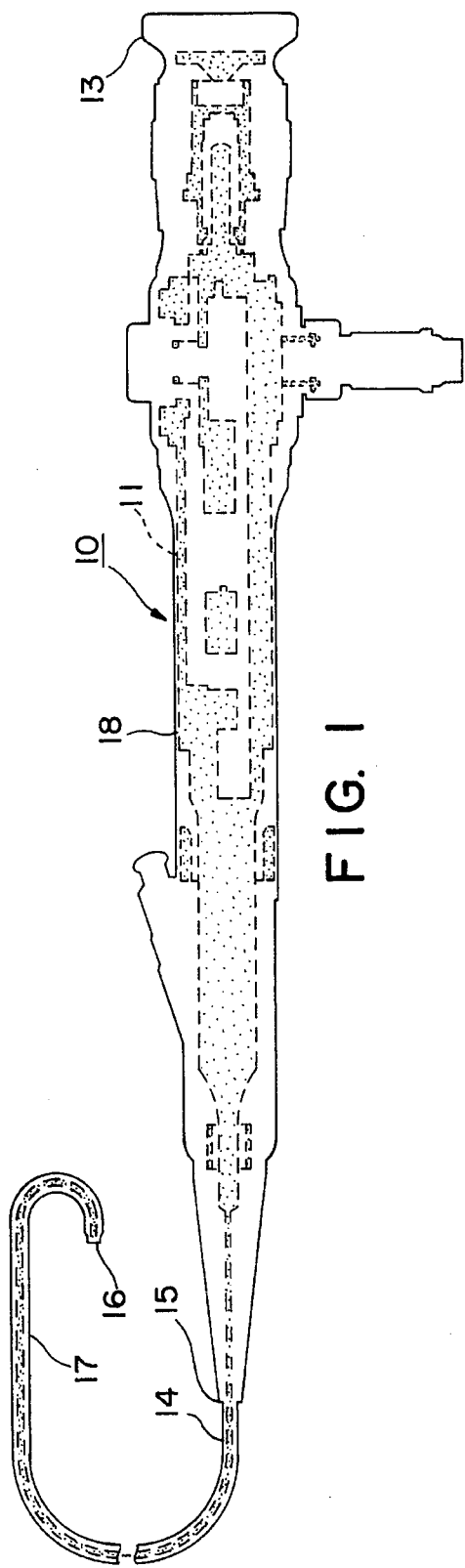
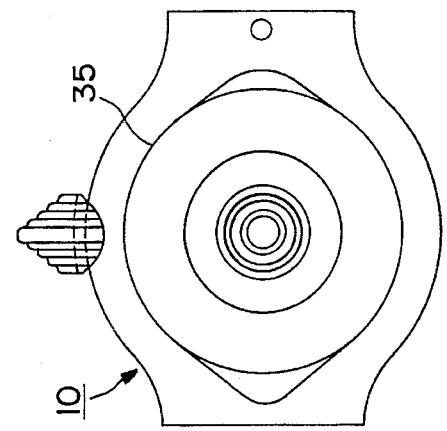
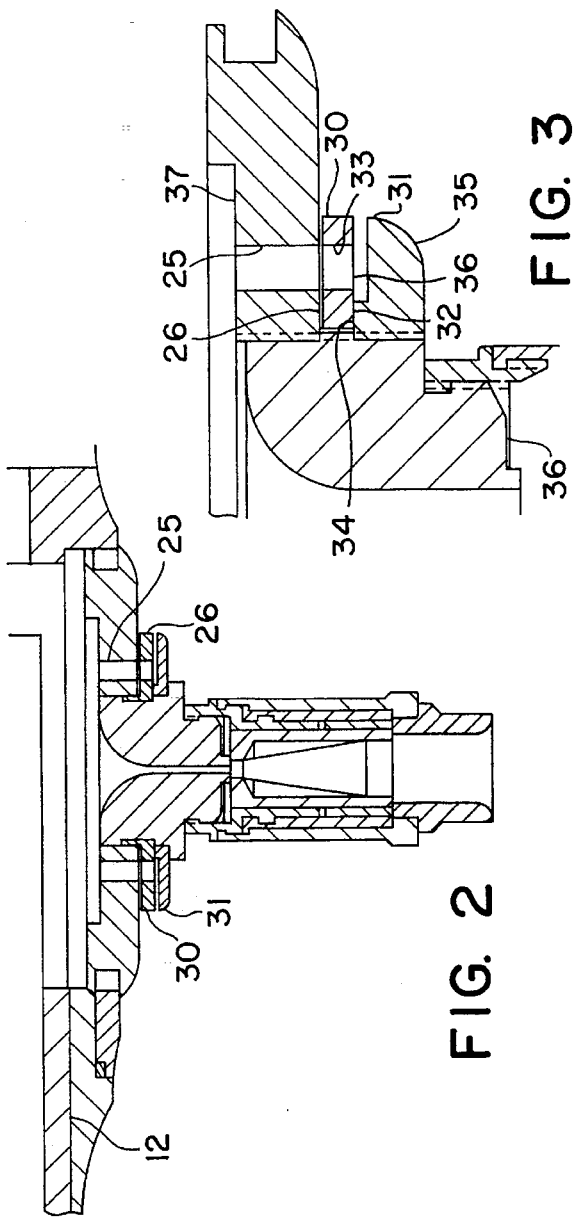

VENT SYSTEM FOR ENDOSCOPES

FIELD OF THE INVENTION

A vent system for the interior cavities in an endoscope continuously to equalize the pressure of the gases in these cavities with external usually atmospheric pressure, but to exclude passage of liquids into the cavities.

BACKGROUND OF THE INVENTION

Endoscopes are surgical instruments which by their nature include substantial interior cavities. These cavities are closed by the instrument's outer structure. These instruments are small, quite delicate, and can have pressure-compliant parts. Substantial differential pressure between the contained gases and the outside gases can damage the instruments. For example, if the compliant part is a balloon or flexible membrane, it may be ruptured.

One of the problems, although not the only one, arises when the instrument is shipped by air. The large pressure differential between gases trapped in the instrument and the lesser atmospheric pressure at high altitude is potentially very destructive. In a similar way during gas sterilization, the instrument is subjected to over-pressure and under-pressure cycles. To prevent damage from these circumstances, endoscopes are provided with an off-on valve which is intended to be closed except when substantial pressure differentials are to be expected such as in shipment by air, or during gas sterilization. Proper use of this valve will prevent any such damage, but because it relies on somebody's attention, the risk exists that person may forget to open the valve when the instrument is to be gas sterilized or is to be shipped.

There is yet another risk. Often the instrument will be subjected to both gas sterilization and liquid soak sterilization. In the former procedure, gas should be allowed to enter the cavities, to prevent pressure induced damage. In the latter it should be closed to exclude liquid during soak sterilization. Liquid never should enter the instrument. If it does, it risks loss of optical clarity in the viewing field and/or damage to the mechanical components of the scope. When an "active" vent is used in the sense of a valve which must be opened and closed, the operator needs to remember to close the vent for the soak operation, and sometimes will forget. This risk is averted by this invention.

It is an object of this invention to provide passive vent means for the internal cavities in an endoscope which will always be open to flow of gas inwardly or outwardly, but which is always closed to flow of liquid into the cavities

BRIEF DESCRIPTION OF THE INVENTION

This invention is carried out in combination with a surgical rigid or flexible endoscope which has a gas impermeable outer structure with internal cavities that are filled with gas. The exterior of the endoscope is exposed to outside pressure, and to both liquids and gases. Because these pressures may be different, the structure can be subjected to a differential pressure between the pressure inside of the structure and the pressure which is outside of the structure.

A vent is formed in the structure which communicates with at least some of the cavities. The vent includes a porous selectively permeable barrier means having pores therethrough of such dimensions and surface properties, both relative to the surface tension property of liquid to be excluded, that the pertinent liquid will not pass through the pores at any anticipated differential pressure, but always will pass pertinent gases. The pores are thus always closed to liquid flow, and are always open to gas flow.

The invention will be fully understood from the following detailed description and the accompanying drawings, in which:

BRIEF DESCRIPTION OF THE DRAWINGS

FIG. 1 is an axial cross-section of a flexible endoscope incorporating the invention, regions subject to pressure differentials being shown in cross-hatch notation;

FIG. 2 is an axial cross-section of a portion of the instrument shown in FIG. 1;

FIG. 3 is an enlarged part of FIG. 2; and

FIG. 4 is a bottom view of FIG. 2.

DETAILED DESCRIPTION OF THE INVENTION

FIG. 1 shows a typical flexible endoscope 10 having a rounded grip 11 formed on underlying structure 12, extending from an eyepiece 13 to a flexible probe 14 having a proximal end 15 and a distal end 16.

Major portions of the probe have a flexible elastic covering 17, especially near its distal end. The purpose of this flexibility is to enable the tip to be bent in order to pass through turns and bends in internal body passages. Inside of the sealed portions of the structure, and of the covering, there are many cavities 18 (air pockets) which contain gas. This provides a structure which can be closed to outside gases. However, should the instrument not be vented during shipment by air or during gas sterilization (when there are alternately under-and over pressure cycles), the covering and other compliant parts can be distorted and damaged. Should the vent not be closed during soak sterilization, then fluid will leak into the cavities and will reduce the clarity of the field of view. All of these situations require specific attention to proper opening or closing of a vent valve, and is thus subject to human error.

While this invention is illustrated for a flexible endoscope, rigid endoscopes and their mountings can also be susceptible to the same damage. The invention is applicable to them, also.

As shown in FIGS. 2 and 3, a vent port 25 is formed through the structure, opening into the cavities. A selectively permeable barrier means 26 overlays the vent port, so that all fluids- both gas and liquid, must pass through it in order to reach the cavities.

A convenient arrangement is shown in FIGS. 2 and 3 associated with the port for lateral transmission of the image, wherein a pair of shoulders 30,31 shown are spaced apart from one another. Shoulder 31 is formed on a ring 35 that is threaded to adapter 36 which in turn is threaded to the body 37 of the instrument. Barrier 26 is formed as a sheet laid against shoulder 30. A ring-shaped spacer 32 has a central opening 33 aligned with vent port 25. It is pressed by a ledge 34 on the ring against the barrier and holds it in place. The thickness of spacer 32 is such that it leaves a gap 36 between the spacer and shoulder 31. The gap is small enough, perhaps less than 0.5 mm wide, to minimize exposure of the barrier to liquid and to contaminants. Gas can readily reach and pass through the barrier to the vent port 25 through opening 33. The vent port or vent ports can be covered with barrier layers which provide either hydrophobic or hydrophilic properties or both types of properties in alternating layers so as to minimize clogging of the barrier.

The chosen material of the barrier means is porous. It is selected to have properties which will not pass liquids involved in a procedures such as cleaning, liquid or gas sterilization, but will always pass gases which may be involved in such procedures. The most common situation is to provide a vent that is always open to passage of air or of sterilizing gases such as ethylene oxide, but which will prevent the passage of liquids, of which the most common examples are those used in soak sterilization of surgical instruments.

Equally, the vent will always be open to flow of gases when the external and internal pressures are different. This is especially the situation when shipping instruments by air.

The capacity to pass or not to pass a liquid is a function of the surface properties of the barrier material, the size of its pores or openings, and the surface tension properties of the involved liquid. When aqueous solutions are involved, the barrier would be regarded as hydrophobic, as contrasted with hydrophilic properties that could permit passage of the liquid. Because different liquids may be involved, for example isopropyl alcohol, which also must be excluded, the term hydrophobic is too limiting. Also, as to different liquids, the barrier might pass some and stop others. Other liquids must also be excluded, among them being acetic acid, ethyl alcohol, formaldehyde and isopropyl alcohol. These are also "pertinent liquids".

Accordingly, in the generic sense, the intended property instead of being strictly hydrophobic or hydrophilic will be described as capable of stopping a pertinent liquid at appropriate pressure differentials, while still permitting the flow of gas.

A suitable example of a useful material which will resist aqueous solutions and pass gas is sold by Millipore Corporation. This is a hydrophobic membrane of polyvinylidene fluoride (PVDE). It has a pore size between about 0.2 mm and 0.5 mm, preferably about 0.2 mm. This will resist water intrusive pressures on the order of 62 psi, and will enable an air flow of about 1.7 liters per minute per cm2 of filtration area with a differential pressure of about 10 psi and exit pressure of about 14.7 psi at 20 degrees C. Isopropyl alcohol does not wet this material filter in less than about 30 seconds. In this embodiment the barrier material is hydrophobic in the classical sense of the word, even though it will also exclude organic materials such as formaldehyde and various alcohols.

This invention is not to be limited by the embodiments shown in the drawings and described in the description, which are given by way of example and not of limitation, but only in accordance with the scope of the appended claims.

I claim:

1. In an endoscopic instrument having an outer structure which is impermeable to fluids, said structure including internal gas-containing cavities, and some portion which is flexible and liable to be exposed both to gas in said cavities and to gas and to liquids outside of said structure, said structure having a vent port therethrough which interconnects at least some of said cavities to said outside gases, the improvement comprising:

selectively permeable barrier means covering said vent port, said barrier means comprising a layer of porous material with surface properties and pore sizes relative to the surface tension properties of a liquid anticipated to be applied to said barrier means that said barrier means will prevent the flow of liquid through said barrier into said cavities, but still always pass gas into and out said cavities;

said outer structure including an inner and an outer surface, said vent port extending between said inner and outer surfaces, said barrier being applied to said outer surface, a ring-shaped spacer having a central opening aligned with said vent port and bearing against said barrier means;

and an overhanging shoulder on said outer structure which overhangs said spacer, leaving a limited spacing between them for access of fluid to said central opening and thereby to the barrier means.

2. Apparatus according to claim 1 in which said barrier means includes alternate layers of hydrophobic and hydrophilic materials whereby to assure exclusion of water, aqueous solutions, and organic liquids likely to be encountered in the cleaning and sterilizing of surgical instruments.

* * * * *